(12) United States Patent
Ha

(10) Patent No.: US 10,575,987 B2
(45) Date of Patent: Mar. 3, 2020

(54) OPHTHALMIC TREATMENT DEVICE AND CONTROL METHOD THEREFOR

(71) Applicant: LUTRONIC CORPORATION, Goyang (KR)

(72) Inventor: Tae Ho Ha, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 310 days.

(21) Appl. No.: 15/503,691

(22) PCT Filed: Aug. 13, 2015

(86) PCT No.: PCT/KR2015/008518
§ 371 (c)(1),
(2) Date: Feb. 13, 2017

(87) PCT Pub. No.: WO2016/024841
PCT Pub. Date: Feb. 18, 2016

(65) Prior Publication Data
US 2017/0281405 A1      Oct. 5, 2017

(30) Foreign Application Priority Data

Aug. 13, 2014   (KR) ........................ 10-2014-0105377

(51) Int. Cl.
*A61F 9/008* (2006.01)
*A61N 5/06* (2006.01)
(Continued)

(52) U.S. Cl.
CPC .............. *A61F 9/008* (2013.01); *A61B 3/102* (2013.01); *A61B 3/12* (2013.01); *A61N 5/06* (2013.01);
(Continued)

(58) Field of Classification Search
USPC ...................................................... 606/2–19
See application file for complete search history.

(56) References Cited

U.S. PATENT DOCUMENTS 6,267,756 B1   7/2001  Feuerstein et al.
2006/0139572 A1  6/2006  Noda et al.
(Continued)

FOREIGN PATENT DOCUMENTS

JP    2006-006653 A    1/2006
JP    2008-086412 A    4/2008
(Continued)

OTHER PUBLICATIONS

International Search Report for International Patent Application No. PCT/KR2015/008518 filed Aug. 13, 2015.

*Primary Examiner* — Carl H Layno
*Assistant Examiner* — Dacheng Xie

(57) ABSTRACT

The present invention relates to an ophthalmic treatment device and a control method therefor, and provides an ophthalmic treatment device and a control method therefor, the ophthalmic treatment device comprising: a treatment beam irradiation unit for irradiating a therapeutic beam to a fundus oculi; a guide image unit for acquiring a guide image of an area including a position onto which the therapeutic beam is irradiated among the area of the fundus oculi; and a display unit for displaying a fundus oculi image of a patient and the position to which the therapeutic beam is irradiated on the fundus oculi image, using the guide image.

16 Claims, 21 Drawing Sheets

(51) Int. Cl.
    *A61B 3/10* (2006.01)
    *A61B 3/12* (2006.01)
    *A61F 9/007* (2006.01)
(52) U.S. Cl.
    CPC ..... *A61F 9/007* (2013.01); *A61F 2009/00844* (2013.01); *A61F 2009/00863* (2013.01)

(56) References Cited

U.S. PATENT DOCUMENTS

| | | | | |
|---|---|---|---|---|
| 2012/0165799 | A1* | 6/2012 | Yamamoto | A61F 9/00821 |
| | | | | 606/4 |
| 2012/0239015 | A1* | 9/2012 | Liesfeld | A61B 3/12 |
| | | | | 606/4 |
| 2013/0261612 | A1* | 10/2013 | Yokosuka | A61B 3/10 |
| | | | | 606/4 |
| 2013/0317487 | A1* | 11/2013 | Luttrull | A61B 18/20 |
| | | | | 606/5 |
| 2015/0173611 | A1 | 6/2015 | Ha et al. | |

FOREIGN PATENT DOCUMENTS

| | | |
|---|---|---|
| JP | 4501007 B2 | 7/2010 |
| JP | 2012-213634 A | 11/2012 |
| KR | 10-2014-0009847 A | 1/2014 |
| KR | 10-1374295 B1 | 3/2014 |
| WO | WO 01/87181 A2 | 11/2001 |
| WO | WO 2006/022045 A1 | 3/2006 |

\* cited by examiner

OPHTHALMIC TREATMENT DEVICE AND CONTROL METHOD THEREFOR

CROSS REFERENCE TO RELATED APPLICATIONS

The present invention is a U.S. National Stage of PCT/KR2015/008518, filed Aug. 13, 2015, which claims the priority of Korean patent application No. 10-2014-0105377 filed on Aug. 13, 2014, which are incorporated herein by reference.

TECHNICAL FIELD

The present invention relates to an ophthalmic treatment apparatus and a method for controlling the same and, more particularly, to an ophthalmic treatment apparatus capable of performing treatment while checking the position where a laser is radiated while the treatment is performed and a method for controlling the same.

BACKGROUND ART

Recently, treatment technologies using a method for changing the state of a tissue by light energy by radiating light that may be absorbed by a human body tissue to the human body are widely applied. From among the treatment technologies, a treatment apparatus using a laser is widely used in various lesions, such as a skin disease, an eye disease, a nerve disease, a joint disease, and a gynecology disease.

In an ophthalmic treatment apparatus using a laser, a plurality of apparatuses for treating a lesion in the anterior segment of an eye, such as cornea plastic surgery, glaucoma or a cataract surgical operation, has been developed. Recently, an apparatus for treating a variety of types of lesions in the area of the fundus oculi, including macular degeneration, has been developed. Furthermore, such a surgical operation apparatus has also been disclosed in Korean Patent Application Publication No. 10-2014-0009846.

A conventional ophthalmic treatment apparatus is configured to perform treatment while observing a surface tissue, such as the retina which may be checked on the outside using light. In this case, an apparatus for treating a lesion in the area of the fundus oculi is targeted on a tissue (e.g., an RPE cell) located on the inside of the retina. Accordingly, there is a problem in that it is difficult to identify an area to which a treatment beam has already been radiated by observing a retina surface.

DISCLOSURE

Technical Problem

The present invention is for providing an ophthalmic treatment apparatus capable of computing a position where a treatment beam has been radiated and displaying the computed position to a user in performing treatment by radiating a treatment beam to a plurality of positions of the fundus oculi, and a method for controlling the same.

Technical Solution

In order to achieve the object, the present invention provides an ophthalmic treatment apparatus, including a treatment beam radiation unit which radiates a treatment beam to a fundus oculi, a guide image unit which obtains a guide image of an area belonging to the area of the fundus oculi and including a position where the treatment beam has been radiated, and a display unit which displays a fundus image of a patient and the position where the treatment beam has been radiated in the fundus image using the guide image.

In this case, the fundus image shows a wider area of the fundus oculi than the guide image, and the guide image includes information about the position where the treatment beam has been radiated. For example, the guide image may include an image of the treatment beam or an image of an aiming beam for aiming the position where the treatment beam is radiated, wherein the image has been focused on the fundus oculi, or may include an image of a degenerated tissue within a treatment area due to the treatment beam.

Furthermore, the area displayed in the guide image includes a visual field area provided to a user through an eyepiece part, and may be photographed using a beam having a wavelength not corresponding to a visible region.

More specifically, the ophthalmic treatment apparatus further includes a photographing beam source which radiates a photographing beam having a wavelength of an infrared or near-infrared band in the direction of the fundus oculi. The guide image unit may be configured to obtain the guide image using the photographing beam reflected by the fundus oculi. In this case, a plurality of the photographing beam sources may be provided and disposed in the outward direction of a path in which the treatment beam is incident on the fundus oculi.

In addition, the ophthalmic treatment apparatus may further include an illumination beam source which radiates an illumination beam having a wavelength of a visible band in the direction of the fundus oculi so that a user is capable of checking the fundus oculi during treatment and a vision image unit which obtains a vision image corresponding to a visual field checked by the user through an eyepiece part using the illumination beam reflected by the fundus oculi.

In this case, a slit for restricting the amount of the illumination beam or the radiation area of the illumination beam is disposed on one side of the illumination beam source. The vision image is configured to show a narrower area than the guide image.

In this case, the photographing beam and the illumination beam are reflected by the fundus oculi and travel in the same path. Part of the illumination beam passes through a beam splitter disposed on the path and travels to the eyepiece part, and the remainder of the illumination beam and the photographing beam are reflected by the beam splitter and are incident on the guide image unit and the vision image unit, respectively.

Meanwhile, the treatment beam radiation unit may sequentially radiate the treatment beam to a plurality of positions of the fundus oculi, and the display unit may accumulatively display the plurality of positions to which the treatment beam has been radiated in the fundus image.

In this case, for example, the fundus image displayed on the display unit may be a reference image obtained by photographing the fundus oculi of the patient prior to treatment. Furthermore, the ophthalmic treatment apparatus may further include a processor which calculates the coordinates of the position where the treatment beam has been radiated in the reference image by mapping the guide image to the reference image. The display unit may display the reference image and the position where the treatment beam has been radiated in the reference image based on the coordinates.

For another example, the fundus image displayed on the display unit may be a combined image of a plurality of the guide images obtained during treatment. In this case, a processor generates the combined image by combining the plurality of guide images. More specifically, when a new guide image is obtained from the guide image unit, the processor may generate a new combined image by combining an already generated combined image and the new guide image. In this case, the processor may calculate the coordinates of the position where the treatment beam has been radiated in the newly generated combined image, and the display unit may display the position where the treatment beam has been radiated in the newly generated combined image and the combined image based on the coordinates.

Meanwhile, in order to achieve the object, the present invention may provide a method for controlling an ophthalmic treatment apparatus, including the steps of radiating a treatment beam to the fundus oculi of a patient by driving a treatment beam radiation unit, obtaining a guide image of an area to which the treatment beam is radiated, and displaying a fundus image of the patient and a position where the treatment beam has been radiated in the fundus image on a display unit using the guide image.

In this case, the step of obtaining the guide image may include radiating a photographing beam of an infrared or near-infrared wavelength to the fundus oculi and obtaining the guide image using the photographing beam reflected by the fundus oculi.

In this case, the step of obtaining the guide image may be performed substantially simultaneously with the step of radiating the treatment beam. The treatment beam radiation unit may sequentially radiate the treatment beam to a plurality of positions of the fundus oculi, and the display unit may accumulatively display the plurality of positions to which the treatment beam has been radiated in the fundus image.

Advantageous Effects

In accordance with the present invention, there are advantages in that a user can easily check on-going treatment contents and the omission of a treatment position or a problem attributable to redundant treatment can be prevented because a position where a treatment beam has been radiated can be displayed on the display unit in real time whenever the treatment beam is radiated using a guide image.

MODE FOR INVENTION

Hereinafter, ophthalmic treatment apparatuses according to embodiments of the present invention are described in detail with reference to the accompanying drawings. In the following description, a position relation between elements is basically described based on the drawings. Furthermore, the drawings may be magnified and displayed if it is necessary to simplify the structure of the invention or if necessary, for convenience of description. Accordingly, the present invention is not limited thereto. In addition, the invention may be practiced by adding, changing or omitting a variety of types of devices.

In the present embodiment, an ophthalmic treatment apparatus for treating a lesion in the area of the fundus oculi, such as a retina, is described as an example, but the present invention is not limited thereto. It is to be noted that the present embodiment may be applied to various treatment apparatuses for treating lesions present in various tissues, such as the tissue of the anterior segment of an eye and a skin tissue, in addition to the area of the fundus oculi.

Figure 1:
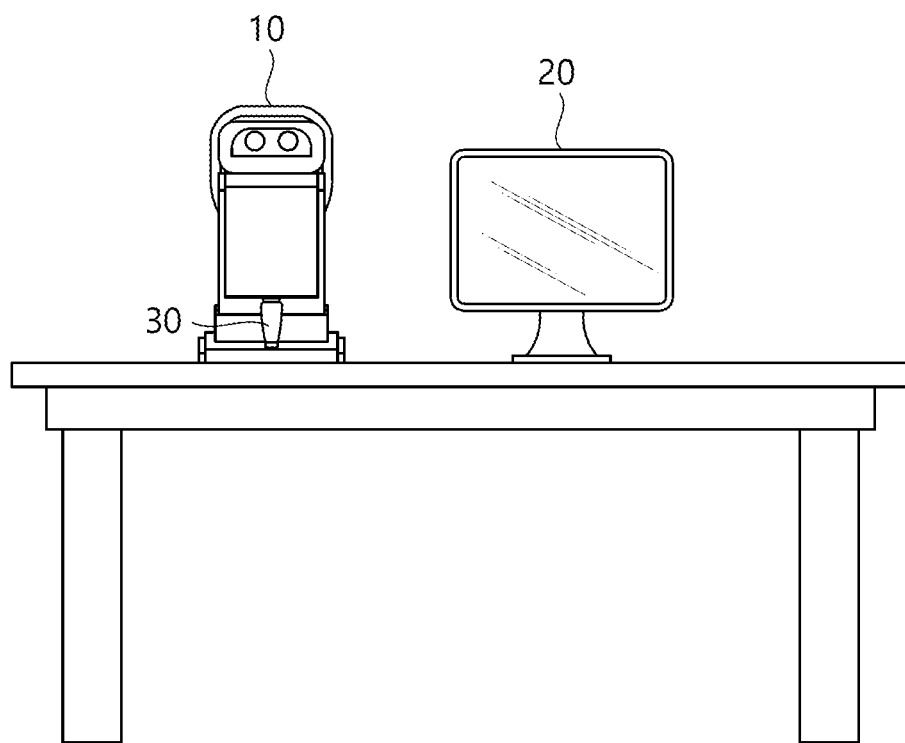
FIG. 1 is a perspective view showing an ophthalmic treatment apparatus according to a first embodiment of the present invention.

FIG. 1 is a perspective view showing an ophthalmic treatment apparatus according to a first embodiment of the present invention. As shown in FIG. 1, the ophthalmic treatment apparatus according to the present embodiment is configured to include a slit lamp 10 and a display unit 20.

The slit lamp 10 is a device which enables a user to perform treatment while observing an eye of a patient. An object part 120 for fixing the position of an eye of a patient is disposed on one side of the body of the slit lamp 10, and an eyepiece part 110 that enables a user to observe an eye of a patient is disposed on the other side of the body of the slit lamp 10. Various manipulation parts 30 for adjusting a visual field direction or treatment contents being observed by a user may be disposed outside the slit lamp 10. Furthermore, a variety of types of elements may be embedded on the inside of the slit lamp 10.

The display unit 20 is disposed in a position close to the slit lamp, and displays a variety of types of information necessary for a user during treatment. As shown in FIG. 1, the display unit 20 may be configured using a flat panel display device. In addition, the display unit 20 may be configured using various display devices. In FIG. 1, the display unit 20 has been illustrated as being separately disposed on one side of the slit lamp, but may be configured as a head-up display within the slit lamp or may be disposed at various positions by taking user convenience into consideration.

Figure 2:
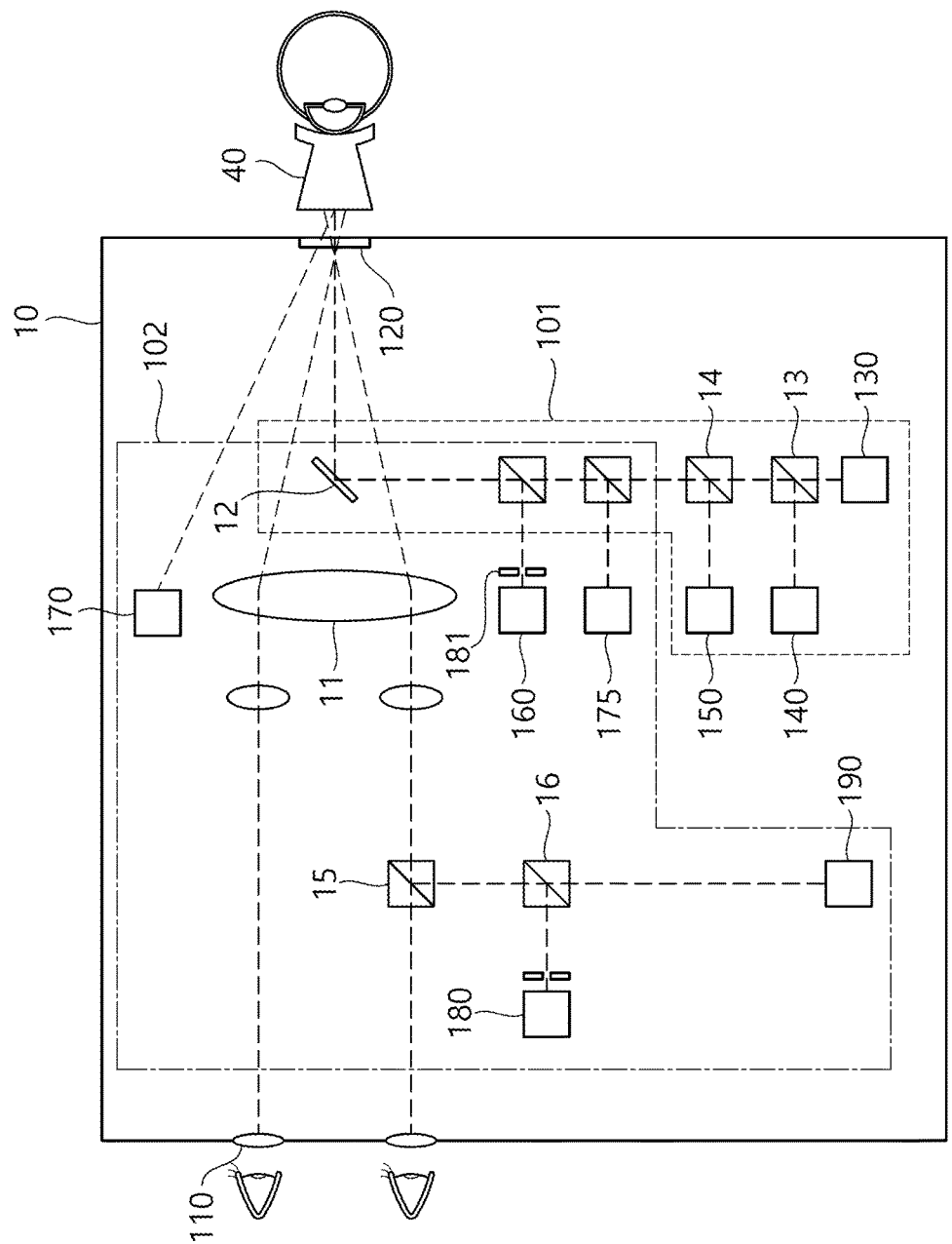
FIG. 2 is a block diagram showing the internal structure of a slit lamp of FIG. 1.

FIG. 2 is a block diagram showing the internal structure of the slit lamp of FIG. 1. As described above, the object part 120 is disposed on one side of the slit lamp 10, and the eyepiece part 110 is disposed on the other side of the slit lamp 10. The object part 120 corresponds to the position where light generated within the slit lamp 10 is incident on the fundus oculi of a patient. A contact lens 40 coming into contact with an eyeball of a patient may be disposed at a position adjacent to the object part 120. In this case, the contact lens may be installed on the slit lamp and may be configured as a unit separated from the slit lamp so that a user can directly bring the contact lens into contact with an eyeball of a patient by grasping the contact lens. The eyepiece part 110 corresponds to a position at which part of or the entire light reflected by the fundus oculi of a patient arrives. A user can observe the fundus oculi of a patient through the eyepiece part. Furthermore, a variety of types of elements, such as a variety of types of light sources, a plurality of optical devices, and a variety of types of detection devices, are disposed between the object part 120 and the eyepiece part 110. Such elements may be basically classified into a treatment optical system 101 and an observation optical system 102 depending on their roles. However, such classification is not exclusive. Some of the elements may correspond to both the treatment optical system and the observation optical system.

First, the treatment optical system 101 is an optical system used to treat a lesion of a patient and to monitor the treatment contents. The treatment optical system includes a treatment beam radiation unit 130 for radiating a treatment beam, an aiming beam radiation unit 150 for radiating an aiming beam, and a monitoring unit 140 for sensing information about the state of the area to which a treatment beam has been radiated during treatment. Furthermore, the treatment optical system may be configured to include a variety of types of optical devices which form a light path in which a treatment beam and an aiming beam travel and a scanner 12 for changing the direction in which a beam travel.

The treatment beam radiation unit 130 is configured to include a treatment beam light source which generates a treatment beam and a variety of types of optical devices (not shown) which processes the light characteristics of a treatment beam. The treatment beam includes a laser, and the treatment beam light source may be configured to include a laser medium or laser diode, such as Nd:YAG or Ho:YAG which can oscillate a laser. Furthermore, the treatment beam radiation unit 130 may include various elements, such as a variety of types of electrical circuits for exciting a laser, an optical filter for oscillating light of a specific wavelength band, and a shutter.

The ophthalmic treatment apparatus according to the present embodiment includes an apparatus for treating a lesion in the area of the fundus oculi, such as macular degeneration, using a selective retina therapy (SRT) method. Accordingly, a treatment beam has the width of a wavelength or pulse which may be selectively absorbed into an RPE cell layer that belongs to a retina tissue having a multi-layer structure and that is located inside by a specific depth from a surface of the retina (a surface capable of being observed through the eyepiece part).

More specifically, the treatment beam radiation unit 130 according to the present embodiment radiates a treatment beam having a visible or near-infrared region wavelength. The treatment beam may pass through a cell layer (based on a retina surface) located at the front of the retina without being almost absorbed into the cell layer, and may be then absorbed into the melanosome of the RPE cell layer located on the inside of the retina. Accordingly, as the amount of energy absorbed by the treatment beam increases, the state of the RPE cell is changed and thus treatment is performed in such a manner that a new RPE cell is regenerated. The reason for this is that a micro bubble is generated in a surface of the melanosome as the temperature of the melanosome rises, and as the micro bubble gradually grows, the RPE cell becomes selectively necrotic and a new RPE cell is regenerated at a corresponding position.

As described above, in the present embodiment, the ophthalmic treatment apparatus is configured to radiate a treatment beam using the SRT method, but the present invention is not limited thereto. The ophthalmic treatment apparatus may be applied to cases where a treatment beam is radiated using various methods, such as a sub-threshold laser method and a micro pulse laser method.

Meanwhile, the aiming beam radiation unit 150 is an element which generates an aiming beam and radiates it to a treatment area. An aiming beam is directly radiated to a treatment area before a treatment beam is radiated or while the treatment beam is radiated, thereby notifying a user of the position where the treatment beam is radiated. The aiming beam may have a wavelength of a visible band so that a person who performs operation can check the aiming beam with the naked eye.

The aiming beam radiated by the aiming beam radiation unit 150 may be radiated in a single spot form in order to indicate one target position where a treatment beam is radiated and may be radiated in the form of a plurality of spots in order to indicate a plurality of positions to which treatment beams are sequentially radiated. In addition, the aiming beam may be radiated in various manners, such as indicating the boundary of the area to which a treatment beam is radiated, in addition to a lattice form.

Furthermore, the monitoring unit 140 is an element for sensing information about the state of a tissue, that is, a target, when a treatment beam is radiated. If an excessively large amount of a treatment beam is radiated, there is a danger that even a neighboring RPE cell or neighboring light-receiving cell may be thermally damaged in addition to an RPE cell, that is, a target. Accordingly, the monitoring unit 140 may sense tissue state information at a position where a treatment beam is radiated while the treatment beam is radiated in real time. The contents of the operation of the treatment beam radiation unit 130 may be controlled based on the tissue state information.

In this case, the state information includes at least one of a change in the temperature of a target tissue, a change in the volume, a change in the refractive index, a movement of a cell, and information regarding a signal generated due to a movement of the cell. Furthermore, the monitoring unit 140 may be designed in various ways in order to sense such state information.

For example, as in an optical coherent tomography (OCT) apparatus, the monitoring unit 140 according to the present embodiment may be configured to sense information about the state of a tissue using interference information between a reference beam and an inspection beam generated by the monitoring unit. More specifically, the reference beam travels along a predetermined path. The inspection beam is radiated to a target position along the path in which a treatment beam is radiated, reflected by the target position and then received by the monitoring unit 140. In this case, as treatment is in progress, the state information of a target tissue is changed and the light path characteristic of the inspection beam is changed, thereby resulting in a change in detected interference information. Accordingly, a change in the state information of a target position can be monitored by sensing a change in interference information by radiating a plurality of inspection beams to a target position while radiating a plurality of treatment beams to the same position.

More specifically, in the present embodiment, the monitoring unit 140 may be configured to extract information, corresponding to the depth area of a target position, from speckle pattern information obtained from interference information and to sense a change in the state of a tissue by continuously performing a comparison between the amounts of a change in extracted information. However, this is only an example. In addition, the monitoring unit may be implemented in various manners, such as sensing information about a change in the state of a tissue using an optical method, like a fundus oculi camera, and sensing a signal generated due to a change in the state of a tissue when a treatment beam is radiated using a sound wave sensor, an ultrasonic sensor or a temperature sensor.

As shown in FIG. 1, the aforementioned treatment beam, aiming beam and inspection beam travel along the same light path through optical devices, such as beam splitters 13 and 14, and are radiated to the fundus oculi of a patient through the object part 120. The scanner 12 is disposed on such a light path. A control unit controls the operation of the scanner 12, and thus a target position to which a treatment beam, an aiming beam, and an inspection beam are radiated can be adjusted.

Meanwhile, the observation optical system 102 is an element which obtains an image of a corresponding position so that a user can check information about the lesion position of a patient and the position on which treatment is performed directly/indirectly. The observation optical system 102 is configured to include an illumination beam source 160 which generates an illumination beam radiated to the fundus oculi of a patient, a vision image unit 180 which obtains a fundus image of the patient using the illumination beam, a photographing beam source 170 which generates a photographing beam, and a guide image unit 190 which obtains a fundus image of the patient using the photographing beam. Furthermore, the observation optical system 102 may further a plurality of optical devices forming a path in which an illumination beam and a photographing beam travel.

First, the illumination beam source 160 generates an illumination beam radiated to the fundus oculi of a patient. As shown in FIG. 2, an illumination beam generated by the illumination beam source 160 is radiated to the fundus oculi of a patient along the light path formed by a plurality of optical devices and then reflected, and travels in the direction of the eyepiece part 110. A user may secure the visual field of a treatment area using the illumination beam reflected through the eyepiece part 110. Accordingly, the user can observe the treatment area while moving the provided visual field, and can manipulate the apparatus so that a treatment beam is radiated while checking the position of an image on which the aforementioned aiming beam is focused in the treatment area.

The illumination beam generated by the illumination beam source 160 has light of a visible band wavelength which can be recognized by a user with the naked eye. More specifically, the illumination beam is configured to have light having a wavelength in the range of 400 nm to 700 nm. For example, in the present embodiment, the illumination beam source 160 may be configured using a light-emitting device which radiates white light.

The illumination beam source 160 generates an illumination beam with limited brightness in order to prevent an excessively large amount of an illumination beam from reaching the eyepiece part. If an illumination beam that reaches the eyepiece part 110 is excessively bright, there are problems in that it is difficult to sense a position where a treatment beam is radiated because it is difficult to identify an image of an aiming beam focused on the fundus oculi and power of concentration is reduced because a degree of fatigue of an eye of a user is increased.

Accordingly, the illumination beam source according to the present embodiment may be configured to generate an illumination beam with relatively low power. Furthermore, a slit 181 may be additionally disposed at a position adjacent to the illumination beam source. The slit may provide a visual field for only a treatment area to which a treatment beam is radiated by reducing the cross section of an on-going illumination beam.

Figure 3A:
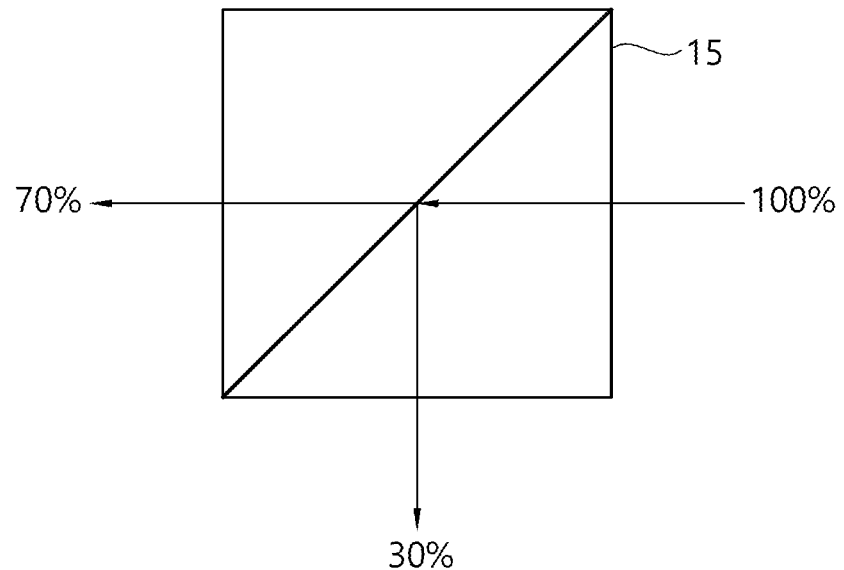
FIGS. 3A and 3B are a diagram showing a light path that passes through a beam splitter of FIG. 2.

Meanwhile, the vision image unit 180 is an element which obtains a vision image using the aforementioned illumination beam. As shown in FIG. 2, part of an illumination beam reflected by the fundus oculi may reach the eyepiece part through a beam splitter 15, and the remaining beam may be reflected by the beam splitter 15 and transferred to the vision image unit (refer to FIG. 3A, an illumination beam of 70% has been illustrated as traveling to the eyepiece part and an illumination beam of 30% has been illustrated as traveling in the direction of the vision image unit). The vision image unit 180 includes an imaging device capable of detecting an illumination beam of a visible band wavelength, and may obtain a vision image. Such a vision image is an image corresponding to a visual field which can be checked by a user through the eyepiece part 110, and is an image in the area substantially identical with the visual field of a user (However, the vision image may be different if a separate slit is disposed in the eyepiece part). Accordingly, the vision image obtained by the vision image unit 180 may be provided to a user or a patient through the display unit 20 and may be stored in a separate database (not shown) and also be used as a treatment record.

In the ophthalmic treatment apparatus which performs treatment using the SRT method, sub-threshold method or micro pulse laser method as described above, however, the target position of a treatment beam is located inside a retina. Furthermore, although degeneration is generated in the tissue of a target position due to a treatment beam, such a state is rarely monitored in the retina surface. Accordingly, it is difficult for a user to identify the position where the treatment beam has been radiated by observing the state through the eyepiece part. For this reason, if a treatment beam is radiated to a plurality of positions, there is a possibility that treatment may be redundantly performed on the same position because it is impossible to check the position to which the treatment beam has already been radiated and there is a difficulty in checking a treatment position after treatment resumes after it is paused.

Accordingly, the ophthalmic treatment apparatus according to the present embodiment is configured to further include the photographing beam source 170 and the guide image unit 190. In this case, the photographing beam source 170 and the guide image unit 190 may obtain guide images while treatment is performed, and may display the position at which a treatment beam has already been radiated on the display unit 20 using the guide images for a user.

In this case, to use the guide image is meant to include both a case where the position is displayed for the user using the guide image itself and a case where information obtained through the guide image is processed and displayed for the user. Furthermore, a method for displaying a position for a user may be configured to display the position to which a treatment beam has already been radiated on a fundus image (display image) displayed on the display unit.

More specifically, in the present embodiment, a reference image captured from the fundus oculi of a patient prior to treatment may be used as fundus image displayed on the display unit. Furthermore, the aforementioned guide image may be captured to include information about a position where a treatment beam is radiated. Accordingly, the photographed area of a guide image can be identified on a reference image by matching the guide image with the reference image, and thus a position where a treatment beam has been radiated can be displayed on the reference image. In accordance with such a method, the ophthalmic treatment apparatus according to the present embodiment can obtain a guide image at each of points of time at which a plurality of treatment beams is radiated and can accumulatively display the position where the treatment beam has been radiated on a reference image of the display unit 20 using the guide image.

More specifically, the photographing beam source 170 radiates a photographing beam. As shown in FIG. 1, the photographing beam source 170 is disposed outside an object lens 11 corresponding to the light path. In FIG. 1, a single photographing beam source has been illustrated as being disposed, but a plurality of the photographing beam sources may be disposed along the circumference outside the object lens. In this case, the photographing beam source 170 can obtain a sharper guide image than a vision image by radiating a larger amount of light to a treatment area, compared to the illumination beam source 160.

Figure 3B:
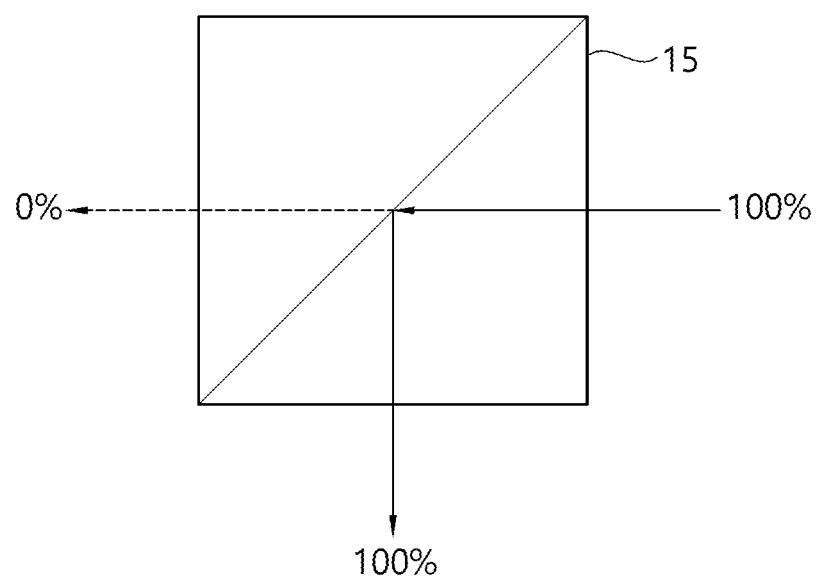

A photographing beam radiated by the photographing beam source 170 is radiated to the fundus oculi of a patient through the object part 120. The photographing beam reflected by the fundus oculi is reflected along the same path as the reflection path of an illumination beam. Furthermore, the photographing beam is reflected by the beam splitter 15 disposed on the reflection path and received by the guide image unit 190 (refer to FIG. 3B, a photographing beam of 100% has been illustrated as traveling in the direction of the vision image unit).

Light of a wavelength that deviates from a visible area may be used as a photographing beam radiated by the photographing beam source 170. In this case, although part of the photographing beam travels in the direction of the eyepiece part without being reflected by the beam splitter 15, it may not hinder the visual field of a user. Accordingly, the photographing beam source 170 may be configured to radiate a photographing beam of an infrared or near-infrared region wavelength of 700 nm or more. More specifically, in the present embodiment, the photographing beam source 170 is configured to radiate a photographing beam having a wavelength in the range of 800 nm to 900 nm.

Furthermore, the guide image unit 190 is configured to include an imaging device for obtaining a guide image by receiving a reflected photographing beam. In this case, the vision image unit 180 is configured to include the imaging device capable of detecting only light of a visible region so that the same vision image as the visual field of a user can be obtained. In contrast, the guide image unit 190 may be configured to include an imaging device capable of detecting light of a visible region in addition to light of an infrared or near-infrared region corresponding to a photographing beam. Accordingly, the guide image unit can obtain an image of a visible region according to an illumination beam in addition to an image of a near-infrared or an infrared region according to a photographing beam.

In this case, an aiming beam and a treatment beam may be displayed in a guide image up to the position on which the fundus oculi has been focused (for reference, a beam splitter 16 adjacent to the vision image unit 180 and the guide image unit 190 distributes part of light incident thereon in the direction of the vision image unit 180 and distributes the remaining light in the direction of the guide image unit 190). Furthermore, a beam having a wavelength of an infrared or near-infrared region has excellent tissue transmission compared to a beam having a wavelength of a visible region, and thus can be displayed on a guide image even up to an image of a target position that has been thermally damaged on the inside of a treatment area.

If a position where a treatment beam has been radiated is to be determined using the position on which the aiming beam or treatment beam has been focused or the thermally damaged image, there may be a difficulty in performing subsequent image computation because the corresponding position may not be sharply displayed in the guide image. Accordingly, in the present embodiment, a separate guide aiming beam source 175 may be configured to be further included so that a position where a treatment beam has been radiated can be easily checked in a guide image.

The guide aiming beam source 175 is an element for radiating a guide aiming beam to a position where a treatment beam is radiated, like the aiming beam radiated by the aiming beam radiation unit. As shown in FIG. 2, the guide aiming beam is radiated to a treatment area along the path in which the treatment beam and the aiming beam are radiated. A guide aiming beam reflected by the treatment area is received by the guide image unit 190.

The guide aiming beam source radiates a beam having a wavelength of an infrared or near-infrared region and having a cross section of a spot form. The position where a treatment beam has been radiated can be sharply displayed in a guide image obtained by the guide image unit due to such a guide aiming beam. In this case, the guide aiming beam may be configured to have a wavelength different from that of a photographing beam radiated by the photographing beam source. Accordingly, a position where a treatment beam is radiated can be easily identified from an image of a treatment area, obtained by a photographing beam, in a guide image.

Figure 4A:
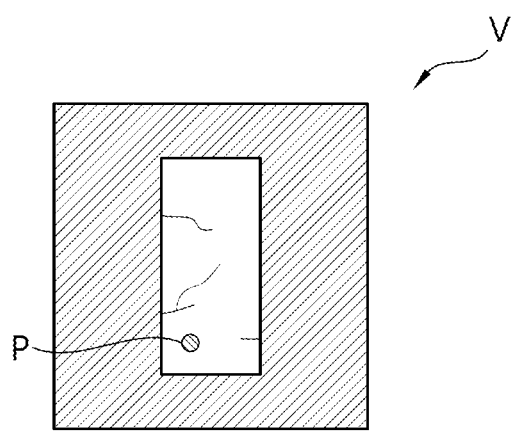
FIGS. 4A and 4B are a diagram showing an example of a vision image and a guide image in FIG. 2.
Figure 4B:
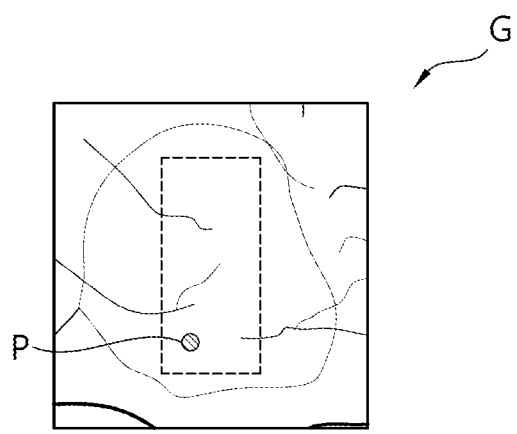

FIGS. 4A and 4B are a diagram showing an example of a vision image and a guide image in FIG. 2. The vision image and the guide image are described through a comparison with reference to FIGS. 4A and 4B.

As shown in FIG. 4A, the vision image V shows only a shape of some region at the center of a visual field which can be checked through the eyepiece part 110. The reason for this is that as described above, an area that belongs to the area of the fundus oculi and to which an illumination beam is radiated is restricted by the slit 181 disposed in the illumination beam source. Accordingly, a user can intensively observe the location of a lesion. However, since the amount of light of the illumination beam source is limited, sharpness is reduced compared to the guide image G.

A position P to which a treatment beam is radiated may appear in the vision image. If a treatment beam has a wavelength of a visible region, an image of the treatment beam that has been focused on the fundus oculi may be displayed in a vision image. Alternatively, if a treatment beam has a wavelength of an infrared or near-infrared region, the position where the treatment beam is radiated can be checked based on an image of an aiming beam focused on the fundus oculi because the image is displayed in a vision image.

Meanwhile, as shown in FIG. 4B, the guide image G displays an image of the area of the fundus oculi which is wider than the vision image, including a treatment area displayed in the vision image. The reason for this is that a separate slit that restricts the cross section of a photographing beam is not installed on the photographing beam source, unlike in the illumination beam source on which the slit has been installed. Furthermore, a shape of the treatment area is displayed in the guide image G more sharply compared to the vision image V because a plurality of the photographing beam sources radiates a sufficient amount of light to the fundus oculi.

Furthermore, a position P to which a treatment beam is radiated is also displayed in the guide image. As described above, a guide aiming beam is radiated to the same position as a treatment beam, and an image of the guide aiming beam focused on the corresponding position is displayed in a guide image. Accordingly, a position where a treatment beam is radiated can be checked based on the displayed image.

As described above, in the present embodiment, the photographing beam source 170 and the guide image unit 190 are additionally provided in order to obtain a guide image. For another example, mapping with a reference image may be possible using the vision image unit. However, there may be a difficulty in performing mapping operation with a reference image because the vision image unit has a limited size in the area of the fundus oculi displayed in an image and has low sharpness as described above. Accordingly, there may be an advantage in that mapping operation can be performed more rapidly and accurately if images are mapped by obtaining a separate guide image as in the present embodiment.

Figure 5:
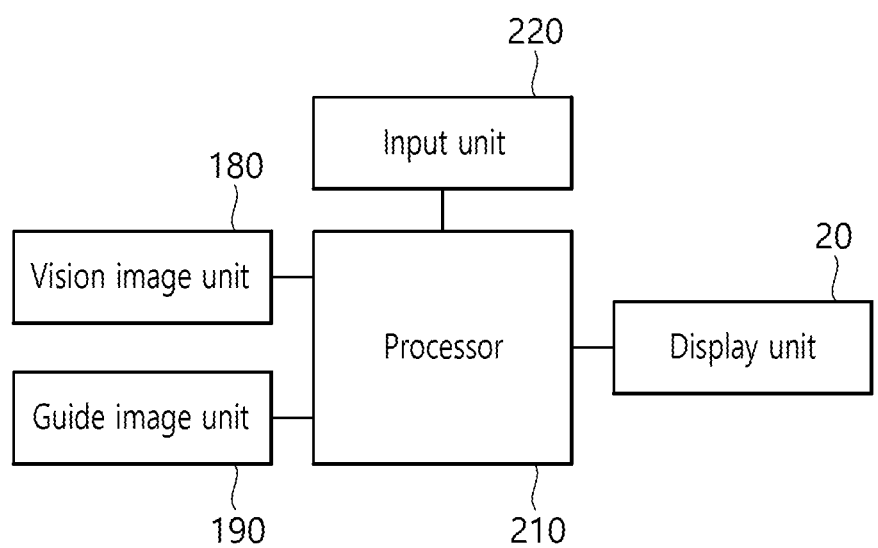
FIG. 5 is a block diagram showing a processor and display unit of FIG. 1.
Figure 6A:
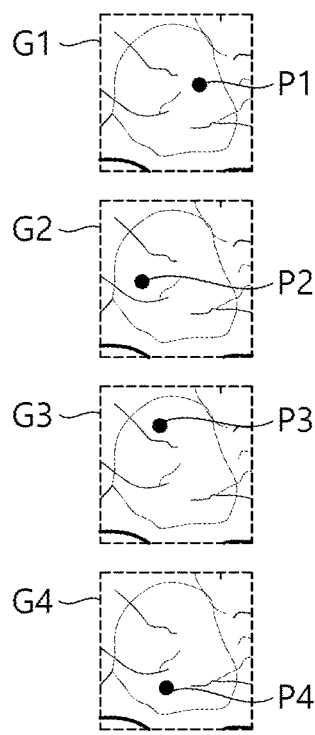
FIGS. 6A and 6B are a diagram showing the matching process of a guide image and a reference image.
Figure 6B:
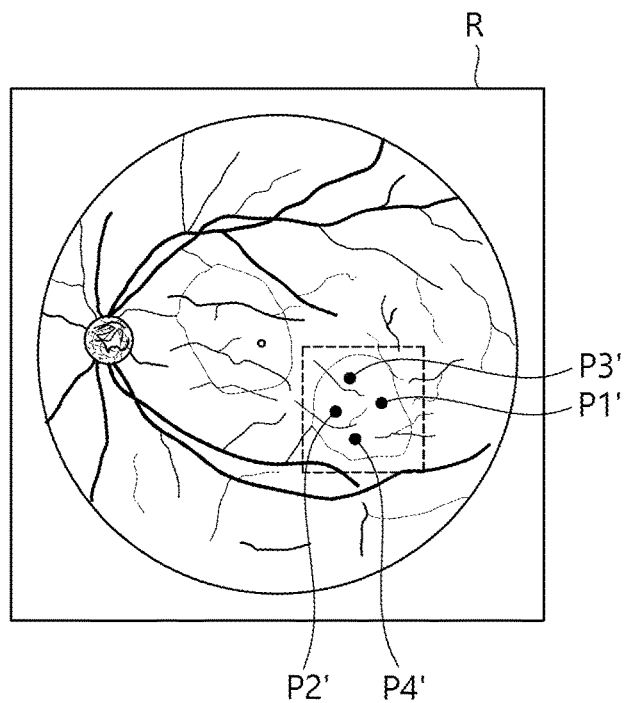

FIG. 5 is a block diagram showing the processor and display unit of FIG. 1. FIGS. 6A and 6B are a diagram showing the matching process of a guide image and a reference image.

As shown in FIG. 5, a vision image and guide image unit obtained by the vision image unit 180 and the guide image unit 190 are provided to a processor 210. A reference image is input from an input unit 220 to the processor 210. The reference image may be a fundus image captured in a step prior to treatment as described above. For example, the reference image is an image captured by a separate diagnostic apparatus using a fundus oculi camera, an OCT apparatus or fluoresce in angiography and may be a single image that displays a wider area of a retina.

In this case, the processor 210 may perform operation for mapping the guide image and the reference image. Furthermore, the processor 210 may compute the coordinates of a position where a treatment beam has been radiated based on the reference image so that the position where the treatment beam has been radiated is displayed in the reference image.

For example, the mapping task of the reference image and the guide image may be performed according to the following method. First, a reference pattern, that is, a criterion, is extracted from the reference image. A reference pattern corresponding to the reference pattern of the reference image is also extracted from the guide image. In this case, the reference pattern is generally distributed in the image, and a tissue having a different shape may be selected depending on its position. For example, in the present embodiment, an image of the blood vessels of the fundus oculi displayed in the reference image and the guide image may be used as the reference pattern. Furthermore, an area displayed in the guide image may be determined in the reference image by analyzing a correlation between the reference pattern of the reference image and the reference pattern of the guide image. In this case, when the correlation between the reference image and the guide image is analyzed, the correlation is not always analyzed from the same position in the reference image, but may be first analyzed from a position having association by taking into consideration a position where a treatment beam has been radiated and the direction or pattern in which the treatment beam is radiated right before. Accordingly, when the area displayed in the guide image is determined in the reference image, the coordinates of a position where a treatment beam has been radiated in the guide image may be calculated, and the coordinates of the position where the treatment beam has been radiated in the reference image may be derived.

However, the method for matching the reference image and the guide image is only an example. In addition, the coordinates of a position where a treatment beam has been radiated may be calculated in various manners using a widely used image processing process.

When the coordinates of the position where the treatment beam has been radiated in the reference image is obtained as described above, the display unit 20 may display the position where the treatment beam has been radiated to a user by indicating the position in the reference image.

FIG. 6A show four sheets of guide images G1, G2, G3, and G4, and FIG. 6B shows a reference image R displayed on the display unit. The four sheets of guide images G1, G2, G3, and G4 may have been obtained at points of time at which treatment beams were radiated, respectively, while the treatment beams were sequentially radiated to four different positions P1, P2, P3, and P4 of the area of the fundus oculi.

When the guide images are obtained as described above, the processor may calculate the coordinates of the position where the treatment beam has been radiated by performing the aforementioned image matching operation. The display unit may accumulatively display the obtained coordinates in the reference image as shown in FIG. 6B (P1', P2', P3', and P4').

Figure 7:
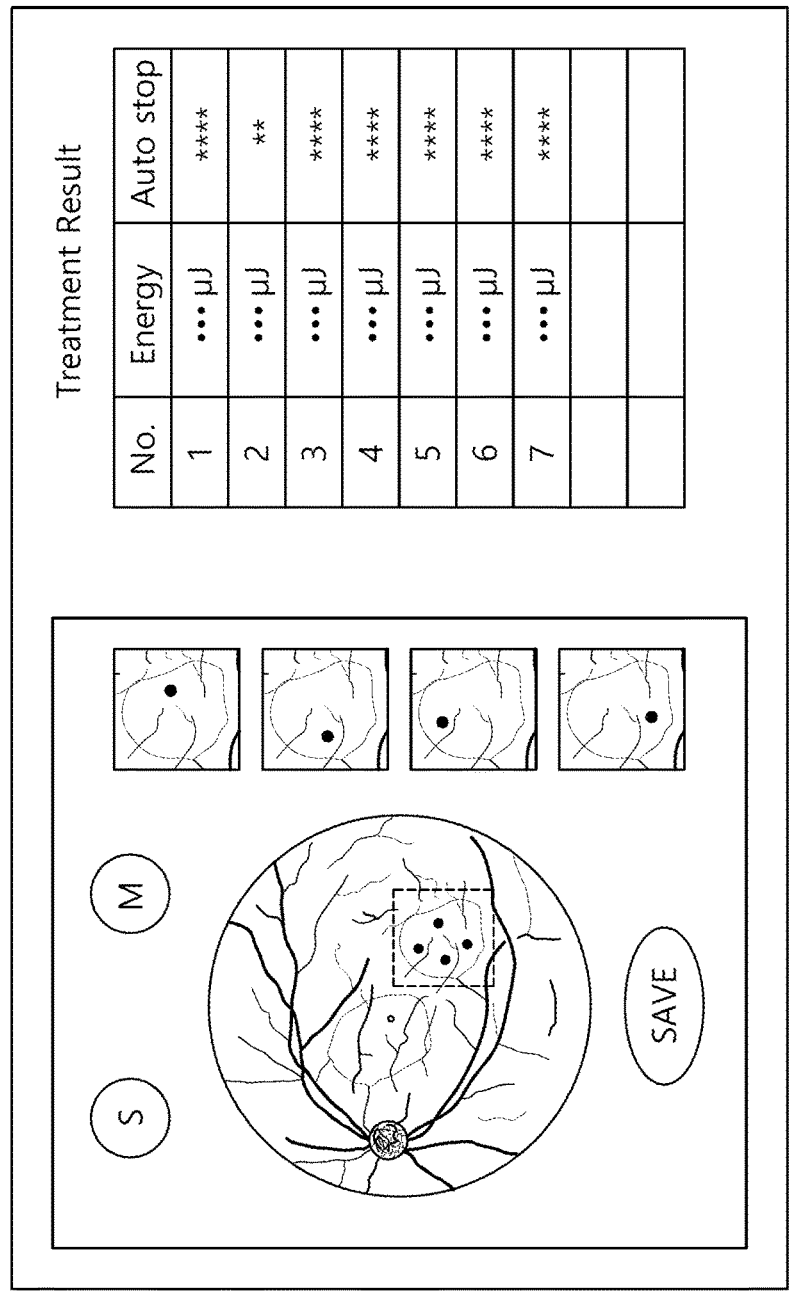
FIG. 7 is a diagram showing an example of an interface shown in a display unit.

FIG. 7 is a diagram showing an example of an interface shown in the display unit. As described above, the display unit 20 may display the reference image to a user. Furthermore, as treatment is in progress, the display unit 20 may notify the user of the positions to which the treatment beams have been radiated by indicating the positions in the reference image. Furthermore, the display unit 20 may receive information about the radiation of the treatment beams from a control unit (not shown) or the treatment beam radiation unit 130, and may display information, such as the number, output, etc. of treatment beams radiated at the respective positions.

Furthermore, the display unit 20 may display a guide image and a vision image provided by the processor 210 depending on a user' selection, may load a data image stored in a separate database unit (e.g., an image captured by a separate device or a previous treatment image of a patient), and may display the loaded data image.

As described above, the ophthalmic treatment apparatus according to the present embodiment can provide information about a position where a treatment beam is radiated, which is difficult to observe through the eyepiece part, to a user through the display unit 20. Accordingly, there are advantages in that redundant treatment or the omission of treatment can be prevented and manipulation convenience can be improved because a user can perform treatment while checking a treatment position through the display unit 20 during treatment.

Meanwhile, in the aforementioned embodiment, the reference image has been illustrated as being captured by a separate diagnostic apparatus. However, the guide image unit of the present embodiment may photograph the fundus oculi of a patient for each section several times, and the processor may generate a reference image by composing the photographed images of the fundus oculi. Furthermore, the ophthalmic treatment apparatus may be configured to directly capture a reference image. Such a configuration is described in more detail based on the following second embodiment. In the following description, in order to avoid the redundancy of a description, contents different from those of the first embodiment are chiefly described.

Figure 8:
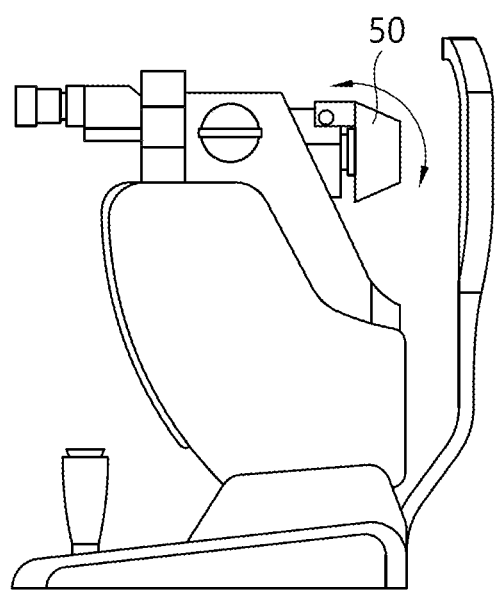
FIG. 8 is a side view showing an ophthalmic treatment apparatus according to a second embodiment of the present invention.
Figure 9A:
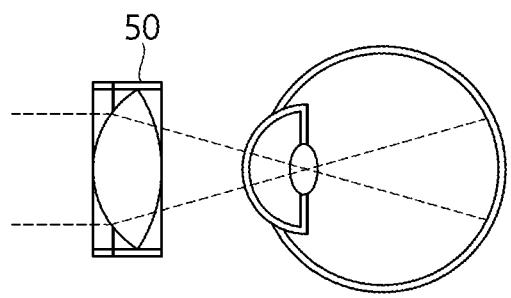
FIGS. 9A and 9B are is a cross-sectional view showing a diagnostic lens and eyepiece of FIG. 8.
Figure 9B:
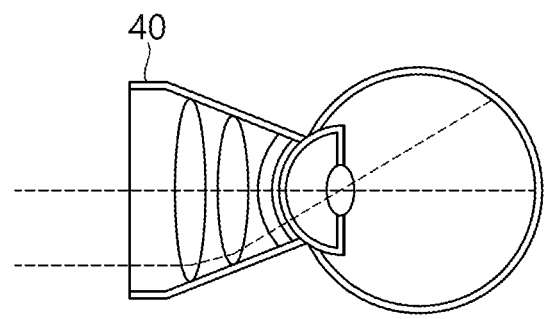

FIG. 8 is a side view showing an ophthalmic treatment apparatus according to a second embodiment of the present invention. FIGS. 9A and 9B are a cross-sectional view showing a diagnostic lens and eyepiece of FIG. 8.

Compared to the aforementioned embodiment, the present embodiment further includes a diagnostic lens 50 capable of directly capturing a reference image. As shown in FIG. 8, the diagnostic lens 50 is disposed adjacent to the object part 120 of the slit lamp. In this case, the diagnostic lens 50 is rotatably disposed on the upper side of the slit lamp 10 by a hinge structure, and may be selectively disposed on the light path between the object part 120 and the fundus oculi of a patient.

FIG. 9A shows a light path passing through the diagnostic lens, and FIG. 9B shows a light path passing through the aforementioned contact lens. As shown in FIGS. 9A and 9B, the contact lens 40 is configured to focus a beam, radiated by the object part 120, near a surface of the fundus oculi of a patient. Accordingly, a treatment beam may be condensed on a target position so that energy is transferred. During treatment, an illumination beam and a photographing beam result in a fundus image having a relatively narrow area. In contrast, the diagnostic lens 50 may obtain a fundus image having a wide area.

Accordingly, when a reference image is captured, the diagnostic lens 50 is disposed on the light path between the object part 120 and the fundus oculi of a patient, and a reference image can be directly captured using the photographing beam source 170 or the illumination beam source 160 (in this case, the slit is removed) (in this case, the contact lens is not disposed on the light path).

Furthermore, when the capturing of the reference image is completed, the diagnostic lens 50 may be upward moved and located outside the light path. The contact lens 40 may be disposed on the light path and treatment may be performed (refer to FIG. 2).

In accordance with the present embodiment, the fundus oculi of a patient can be diagnosed and treated using a single ophthalmic treatment apparatus. Accordingly, there are advantages in that a cost can be reduced and the time taken to diagnose and treat a patient can be reduced.

Figure 10:
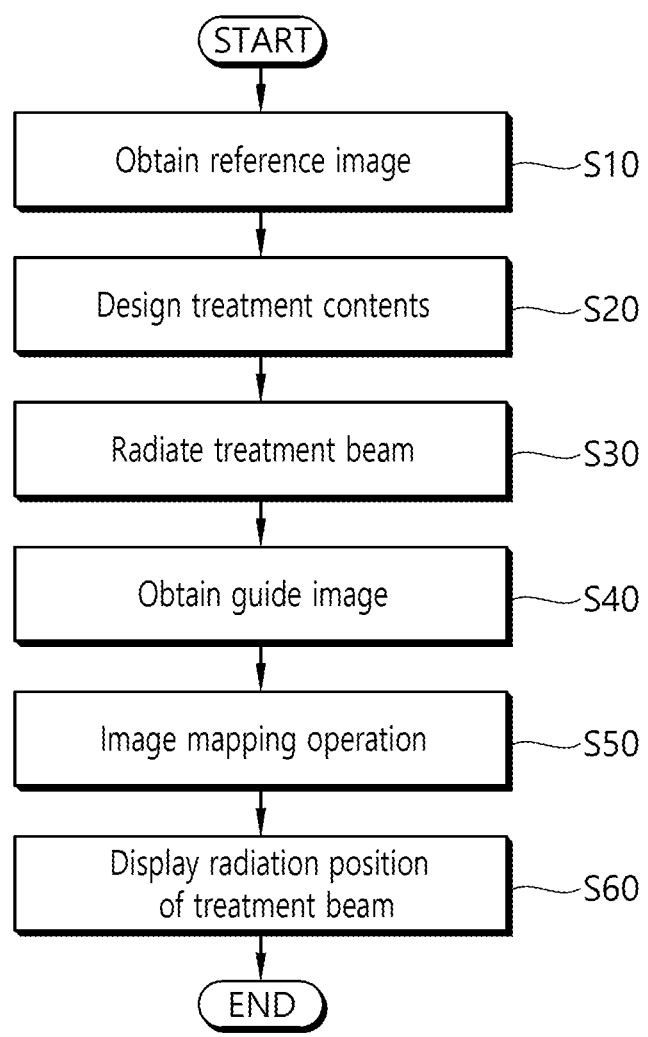
FIG. 10 is a flowchart illustrating a method for controlling the ophthalmic treatment apparatus of FIG. 1.

A method for controlling the ophthalmic treatment apparatus according to the aforementioned first and second embodiments is described with reference to FIG. 10. FIG. 10 is a flowchart illustrating a method for controlling the ophthalmic treatment apparatus of FIG. 1.

As shown in FIG. 10, first, a step of obtaining a reference image is performed (S10). As described above, in the step of obtaining the reference image, as described above, a fundus image captured by a separate diagnostic apparatus may be received or the ophthalmic treatment apparatus itself may obtain the reference image by capturing the reference image or composing images.

When the reference image is obtained, a step of designing the treatment contents is performed (S20). The position and contents of a lesion of a patient may be diagnosed based on a reference image obtained in a previous step, and the treatment contents may be designed based on the diagnosed position and contents. More specifically, a position to which a treatment beam is radiated, a pattern in which the treatment beam is radiated, the amount of energy of the treatment beam and so on may be designed in detail.

When the design of the treatment contents is completed, treatment is performed by radiating a treatment beam (S30). As described above, the control unit radiates the treatment beam to the position of the lesion of the patient by driving the treatment beam radiation unit 130. The treatment beam may be sequentially radiated to a plurality of positions of the fundus oculi depending on a set condition.

While the treatment beam is radiated, a step of obtaining a guide image may be performed (S40). In this step, the guide image unit 190 obtains the guide image using a photographing beam radiated by the photographing beam source 170. In this case, the step of obtaining the guide image may be performed substantially simultaneously with the step of radiating the treatment beam so that an image of an aiming beam focused on a treatment area or an image of the treatment beam is displayed. The step of obtaining the guide image may be simultaneously performed whenever a treatment beam is radiated. If the treatment beam is radiated to a single position several times, the step of obtaining a guide image may be performed once for each position.

Meanwhile, although not separately shown in FIG. 10, while the treatment beam is radiated, an illumination beam is also radiated to the fundus oculi of the patient, and a visual field is provided to a user. A step of obtaining a vision image using such an illumination beam may also be performed.

The guide image and the vision image may be intermittently obtained at the moment when the treatment beam is radiated, but while treatment is performed, the guide image unit and/or the vision image unit may be configured to continuously record the guide image and the vision image, to extract image frames at a necessary point of time, and to use the extracted image frames as the guide image and/or the vision image.

When the guide image is obtained through the aforementioned step, an image mapping operation step is performed (S50). In this step, an image mapping task is performed using the reference image and the guide image obtained in the previous steps. A value obtained by converting the position where the treatment beam has been radiated, displayed in the guide image, into the coordinates of the position in the reference image through the image mapping task. This step is performed by the processor 210, and a detailed description thereof is substituted with that of FIG. 5.

When the image mapping operation task is terminated, a step of displaying the position where the treatment beam has been radiated is performed (S60). The position where the treatment beam has been radiated is displayed in the reference image that is being displayed on the display unit 20. In this case, the position where the treatment beam is displayed may be based on the coordinates of the radiation position calculated in the aforementioned step.

When the treatment beam is radiated to at any position of the treatment area through the above steps, information about the position is displayed on the display unit, the position to which a treatment beam is radiated may be changed, and a treatment step is performed. Accordingly, steps S30 to S60 may be repeatedly performed. As such steps are performed, the user can continue to check the position where the treatment beam is radiated through the display unit while treatment is performed.

The first embodiment and the second embodiment correspond to a configuration in which a reference image captured prior to treatment is displayed on the display unit. In contrast, a fundus image displayed on the display unit may be configured using images obtained during treatment. Such a configuration is described in more detail based on the following third embodiment. In the following description, however, in order to avoid the redundancy of a description, contents different from those of the first and the second embodiments are chiefly described.

Figure 11A:
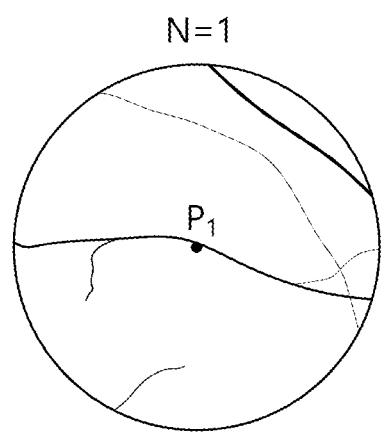
FIGS. 11A, 11B, and 11C show guide images obtained by an ophthalmic treatment apparatus according to a third embodiment of the present invention.
Figure 11B:
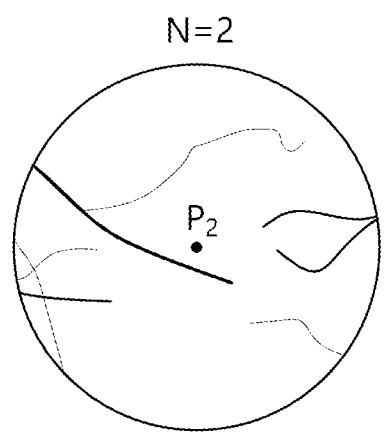
Figure 11C:
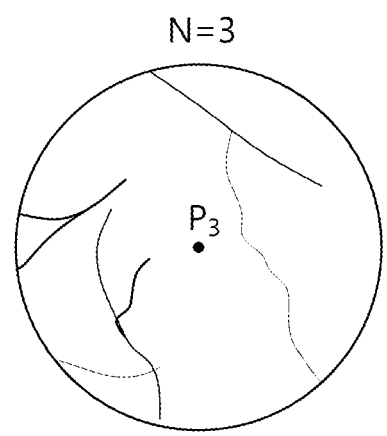
Figure 12A:
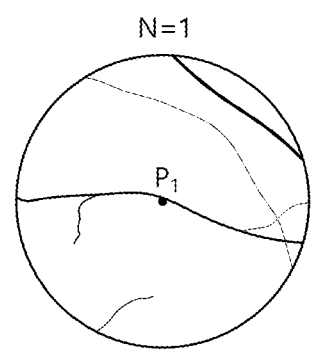
FIGS. 12A, 12B, and 12C show fundus images displayed on a display unit in the third embodiment.
Figure 12B:
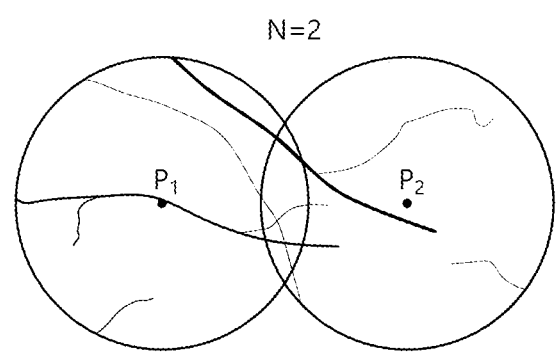
Figure 12C:
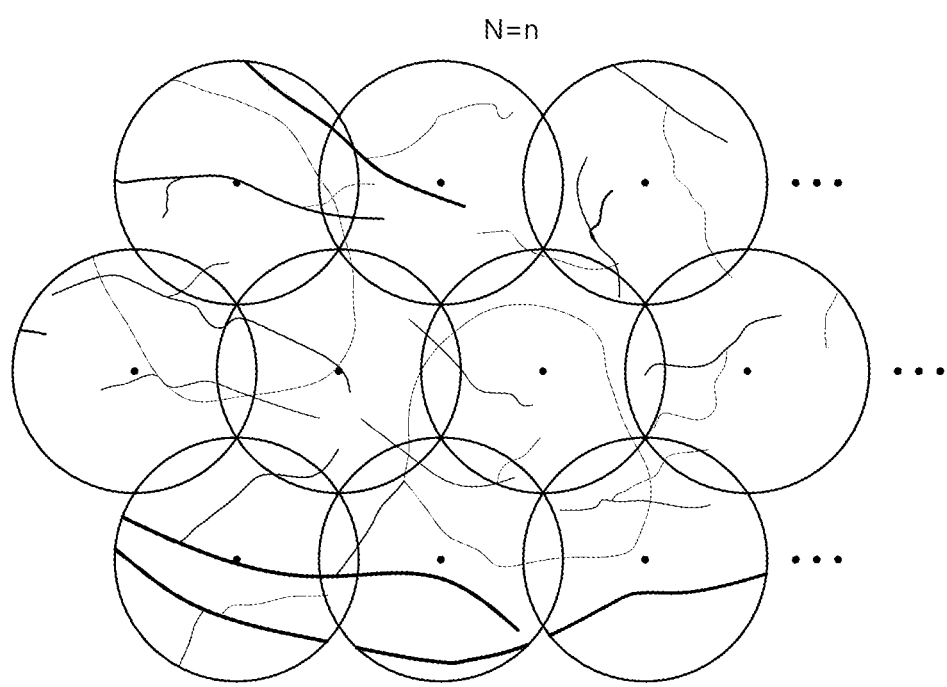

FIGS. 11A, 11B and 11C show guide images obtained by an ophthalmic treatment apparatus according to a third embodiment of the present invention. FIGS. 12A, 12B, and 12C show fundus images displayed on the display unit in the third embodiment.

FIG. 11A is a guide image obtained during treatment at a first treatment position, FIG. 11B is a guide image obtained during treatment at a second treatment position, and FIG. 11C is a guide image obtained during treatment at a third treatment position. As described above, the present ophthalmic treatment apparatus generates a plurality of guide images corresponding to treatment positions, respectively, while treatment is performed. In the present embodiment, in displaying a position where a treatment beam has been radiated on the display unit, a combined image of a plurality of guide images obtained during treatment may be used.

For example, if a treatment beam is radiated to the first treatment position, a fundus image may be displayed on the display unit using the first guide image because one guide image has been obtained. In this case, since the guide image includes information about the position where the treatment beam has been radiated, the position where the treatment beam has been radiated may be displayed on the display unit using the information (refer to FIG. 12A).

Furthermore, if a treatment beam is radiated to the second treatment position, a new fundus image may be generated by combining the guide image obtained the first treatment position and the guide image obtained at the second treatment position. Such a combined image may be generated through analysis of a correlation after extracting a pattern, that is, a reference, from each image as in the method of mapping a reference image and a guide image, which has been described in the previous embodiment. Furthermore, the coordinates of the second treatment position to which the second treatment beam has been radiated may be calculated from the second guide image, and coordinates to be displayed in the combined image may be calculated using the calculated coordinates. Accordingly, the combined image may be displayed on the display unit as a fundus image, and the position where the first treatment beam has been radiated and the position where the second treatment beam has been radiated may be displayed in the fundus image (refer to FIG. 12B).

Likewise, if a treatment beam is radiated to an n-th treatment position, a new fundus image (n-th combined image) may be generated by combining a fundus image combined in a previous step ((n−1)-th) and a newly obtained guide image (n-th guide image). Furthermore, positions where first to n-th treatment beams are radiated may be displayed in the newly generated fundus image (n-th combined image) on the display unit (refer to FIG. 12C).

If a fundus image is displayed on the display unit using images obtained during treatment as described above, there is an advantage in that on-going treatment contents can be dynamically displayed compared to use of a reference image. Furthermore, there is an advantage in that operation necessary to generate a combined image can be rapidly performed because the operation is correlation operation between relatively small areas compared to mapping with a reference image and analysis of the correlation is performed based on a reference disposed in the boundary portion of a previous combined image.

Figure 13:
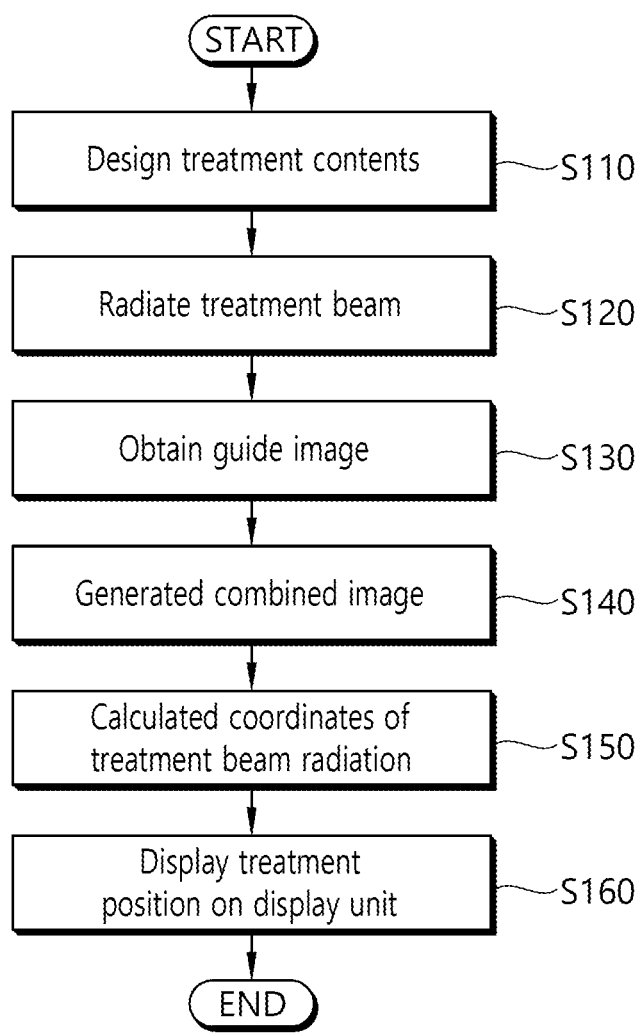
FIG. 13 is a flowchart illustrating a method for controlling the ophthalmic treatment apparatus according to the third embodiment.

A method for controlling the ophthalmic treatment apparatus according to the third embodiment is described below with reference to FIG. 13. FIG. 13 is a flowchart illustrating a method for controlling the ophthalmic treatment apparatus according to the third embodiment.

In accordance with the present embodiment, a step of generating a reference image may be omitted. As shown in FIG. 13, a step of designing treatment contents is performed (S110). When the design of the treatment contents is completed, treatment is performed by radiating a treatment beam based on the designed treatment contents (S120). Furthermore, while the treatment beam is radiated, a step of obtaining a guide image is performed (S130). Such steps are the same as steps S20 to S40 of FIG. 10, and a detailed description thereof is omitted.

When the guide image is obtained through the step, a combined image is generated (S140). In this step, the combined image may be generated by combining a plurality of the guide images obtained during the treatment. However, in the case of a first treatment position, a guide image obtained at the corresponding position is used without any change. In the case of a second treatment position, a combined image may be generated by the previous guide image and a guide image in the current step. Furthermore, from a third treatment position, a new combined image may be generated by combining the previous combined image and a newly obtained combined image.

When the combined image is generated, the coordinates of the positions where the treatment beams have been radiated are calculated (S150). In this step, coordinates in the newly generated combined image may be calculated using information about the position where the treatment beam has been radiated, which is displayed in a newly obtained guide image.

Furthermore, a fundus image may be displayed on the display unit using the newly generated combined image, and the positions where the treatment beams have been radiated may be accumulatively displayed in the fundus image (S160). Furthermore, when a treatment position is changed, steps S120 to S160 may be repeatedly performed.

In the above description, a new combined image has been illustrated as being generated whenever a position to which a treatment beam is radiated is changed, but the present invention is not limited thereto. If a position where a treatment beam has been radiated may be newly displayed in a previous combined image, the step of generating a combined image may be omitted in some treatment positions.

Furthermore, in the present embodiment, in configuring a fundus image using images obtained during treatment, a guide image has been illustrated as being used, but the present invention is not limited thereto. A combined image may be generated using vision images. In this case, however, disadvantages are expected in that sharpness is low and operation is difficult because an obtained area is narrow.

Furthermore, in the present embodiment, a combined image has been illustrated as being displayed. In addition to a combined image, a separate reference image may be received and the combined image and the reference image may be selectively used, if necessary.

Furthermore, although not shown in FIG. 13, when the radiation of the treatment beams to all of the treatment positions is completed, a step of capturing a separate image in which the position of a tissue treated by the treatment beams is displayed and comparing the position of the treated tissue displayed in the separate image with the positions of the treatment beams accumulatively displayed on the display unit may be additionally performed. For example, in the case of a fundus angiography image (FA image) or an OCT image, a position inside a retina that has been thermally damaged by a treatment beam is displayed in the FA image or OCT image. Accordingly, whether treatment has been normally performed can be checked and reliability of the apparatus can be improved because such an image is compared with the position of a treatment beam displayed on the display unit and a result of the comparison is provided to a user.

Meanwhile, in the aforementioned first to third embodiments, the treatment apparatus which treats a lesion generated in the fundus oculi has been chiefly described. However, the present invention is not limited to the treatment apparatus which treats a lesion in the area of the fundus oculi and the method for controlling the same, and may also be applied to the treatment of a lesion other than a lesion in the area of the fundus oculi. For example, in the following fourth embodiment, an example in which the present invention has been applied to a lesion other than the fundus oculi is described. In the following description, however, in order to avoid the redundancy of a description, contents different from those of the aforementioned embodiments are chiefly described.

Figure 14:
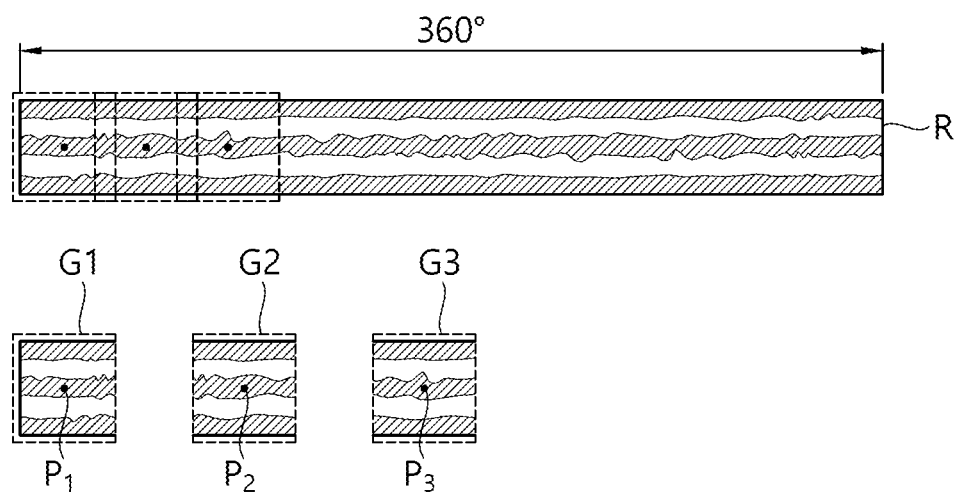
FIG. 14 is a diagram showing the matching process of a guide image and a reference image according to a fourth embodiment of the present invention.

FIG. 14 is a diagram showing the matching process of a guide image and a reference image according to a fourth embodiment of the present invention.

In the present embodiment, an optical treatment apparatus which treats glaucoma by radiating a treatment beam is chiefly described. Glaucoma is a lesion in which the ophthalmic nerve is damaged due to a rise of intraocular pressure. Treatment is performed in such a way as to secure a path in which an intraocular fluid is discharged and to maintain proper intraocular pressure. To this end, in the present invention, treatment may be performed by radiating a treatment beam to a trabecular meshwork (TM) tissue located near the limbus of the anterior segment of an eye using the ophthalmic treatment apparatus according to the present invention and a gonio lens having a reflector.

In such a treatment method, a treatment beam is radiated to a plurality of treatment positions along the TM tissue. As in the aforementioned embodiment, positions where the treatment beams are radiated are displayed on the display unit 20 using guide images G obtained during the treatment.

More specifically, in the present embodiment, as in the aforementioned first embodiment, the position where the treatment beam is radiated can be checked in real time by capturing a reference image of the TM tissue before the treatment is performed and mapping the reference image to the guide image obtained during the treatment.

As shown in FIG. 14, a reference image R is a captured image of part of or the entire section of the TM tissue corresponding to a treatment area. The reference image may have been captured using the gonio lens. More specifically, a two-dimensional image of the TM tissue having a cylindrical form may be captured by rotating the gonio lens or the reflector within the gonio lens and used as the reference image. In addition, a three-dimensional image of the TM tissue captured by a tomographic apparatus, such as an OCT, and may be used as the reference image.

Furthermore, guide images G1, G2, and G3 are images captured during the treatment at the positions where the treatment beams are radiated, respectively, and are images including information about the positions where the treatment beams are radiated. Accordingly, when the positions where treatment beams are radiated are changed, respective guide images may be secured, and positions P1, P2, and P3 where treatment beams have been radiated may be calculated by mapping the corresponding guide images to the reference image. Accordingly, the reference image and the positions where the treatment beams have been radiated can be accumulatively displayed in the reference image on the display unit.

In the above embodiment, in treating glaucoma using treatment beams, the configuration to which the technology for mapping guide images to a reference image and displaying the results on the display unit as in the first embodiment is applied has been chiefly described. As in the second embodiment, however, the technology for combining a plurality of images captured by the ophthalmic treatment apparatus according to the present invention other than a separate photographing apparatus and using a combined image as a reference image may be applied. Furthermore, as in the third embodiment, the technology for sequentially combining guide images captured during treatment and displaying a combined image on the display unit may also be applied.

As described above, the treatment apparatus and the method for controlling the same according to the present invention may be applied to the treatment of various lesions, such as glaucoma treatment, in addition to a lesion of the fundus oculi. Furthermore, the treatment apparatus and the method for controlling the same according to the present invention may also be applied to an optical treatment apparatus which treats lesions at various positions, wherein a position where a treatment beam is radiated is difficult to check, in addition to an eye-related lesion and a method for controlling the same.

One embodiment of the present invention has been described in detail above, but the present invention is not limited to the embodiment. A person having ordinary skill in the art to which the present invention pertains may practice the present invention by modifying or changing the present invention in various ways without departing from the range of the technical characteristic of the present invention defined in the claims.

The invention claimed is:
1. An ophthalmic treatment apparatus, comprising:
   a treatment beam radiation unit which radiates a treatment beam to a fundus;
   a photographing beam source which radiates a photographing beam in a direction of the fundus;
   a guide image unit which obtains a guide image of an area belonging to an area of the fundus and comprising a position where the treatment beam has been radiated, wherein the guide image unit obtains the guide image using the photographing beam reflected by the fundus;
   a processing unit which generates a fundus image of a patient and the position where the treatment beam has been radiated in the fundus image using the guide image; and
   a display unit which displays the fundus image of the patient and the position where the treatment beam has been radiated in the fundus image.
2. The ophthalmic treatment apparatus of claim 1, wherein:

the fundus image shows a wider area of the fundus than the guide image, and the guide image comprises information about the position where the treatment beam has been radiated.

3. The ophthalmic treatment apparatus of claim 1, wherein the guide image comprises an image of at least one of the treatment beam, an aiming beam radiated to the position where the treatment beam is radiated and having a wavelength of a visible region, and a guide aiming beam radiated to the position where the treatment beam is radiated and having a wavelength of an infrared or near-infrared region, the image being focused on the fundus.

4. The ophthalmic treatment apparatus of claim 1, wherein the guide image is captured to comprise a beam having a wavelength of an infrared or near-infrared band.

5. The ophthalmic treatment apparatus of claim 1, wherein a plurality of the photographing beam sources is provided and disposed in an outward direction of a path in which the treatment beam is incident on the fundus.

6. The ophthalmic treatment apparatus of claim 1, further comprising a guide aiming beam source which radiates a guide aiming beam having a wavelength of an infrared or near-infrared band to the position where the treatment beam is radiated, wherein the guide image unit obtains the guide image comprising information about the position where the treatment beam has been radiated using the guide aiming beam reflected from the position where the treatment beam has been radiated.

7. The ophthalmic treatment apparatus of claim 1, further comprising:

an illumination beam source which radiates an illumination beam having a wavelength of a visible band in the direction of the fundus so that a user is capable of checking the fundus during treatment; and a vision image unit which obtains a vision image corresponding to a visual field checked by the user through an eyepiece part using the illumination beam reflected by the fundus.

8. The ophthalmic treatment apparatus of claim 7, wherein:

a slit for restricting an amount of the illumination beam or an radiation area of the illumination beam is disposed on one side of the illumination beam source, and the vision image shows a narrower area than the guide image.

9. The ophthalmic treatment apparatus of claim 7, wherein:

the photographing beam and the illumination beam are reflected by the fundus, part of the illumination beam passes through a first beam splitter and travels to the eyepiece part, and a second beam splitter splits a remainder of the illumination beam and the photographing beam to the guide image unit and to the vision image unit, respectively.

10. The ophthalmic treatment apparatus of claim 1, wherein:

the treatment beam radiation unit sequentially radiates the treatment beam to a plurality of positions of the fundus, and the display unit accumulatively displays the plurality of positions to which the treatment beam has been radiated in the fundus image.

11. The ophthalmic treatment apparatus of claim 1, wherein the fundus image displayed on the display unit is a reference image obtained by photographing the fundus of the patient prior to treatment.

12. The ophthalmic treatment apparatus of claim 11, further comprising a processor which calculates coordinates of the position where the treatment beam has been radiated in the reference image by mapping the guide image to the reference image, wherein the display unit displays the reference image and the position where the treatment beam has been radiated in the reference image based on the coordinates.

13. The ophthalmic treatment apparatus of claim 1, wherein the fundus image displayed on the display unit is a combined image of a plurality of the guide images obtained during treatment.

14. The ophthalmic treatment apparatus of claim 13, further comprising a processor which generates the combined image by combining the plurality of guide images, wherein when a new guide image is obtained from the guide image unit, the processor generates a new combined image by combining an already generated combined image and the new guide image.

15. The ophthalmic treatment apparatus of claim 14, wherein:

the processor calculates coordinates of the position where the treatment beam has been radiated in the newly generated combined image, and the display unit displays the position where the treatment beam has been radiated in the newly generated combined image and the combined image based on the coordinates.

16. The ophthalmic treatment apparatus of claim 1, further comprising a diagnostic lens capable of being selectively disposed on a light path of an object part in which an eyeball of the patient is located, wherein the reference image is the fundus image of the patient captured in a state in which the diagnostic lens has been disposed on the light path.

* * * * *